United States Patent [19]

Papay et al.

[11] 4,225,449
[45] Sep. 30, 1980

[54] LUBRICATING OIL AND FUEL COMPOSITIONS

[75] Inventors: Andrew G. Papay, Manchester; Joseph P. O'Brien, Kirkwood, both of Mo.

[73] Assignee: Edwin Cooper, Inc., St. Louis, Mo.

[21] Appl. No.: 31,620

[22] Filed: Apr. 19, 1979

[51] Int. Cl.$^3$ .............................................. C10M 1/48
[52] U.S. Cl. ........................................ 252/46.6; 44/76; 252/48.2
[58] Field of Search ................... 252/46.6, 48.2; 44/76

[56] References Cited

U.S. PATENT DOCUMENTS

| | | | |
|---|---|---|---|
| 2,470,077 | 5/1949 | Fincke | 252/48.2 X |
| 3,206,401 | 9/1965 | O'Halloran | 252/46.6 |
| 3,208,940 | 9/1965 | Owens et al. | 252/48.2 X |
| 3,449,440 | 6/1969 | Anderson | 252/48.2 X |
| 3,583,915 | 6/1971 | Myers | 252/46.6 |
| 3,591,354 | 7/1971 | Bouffard | 44/76 X |
| 3,807,974 | 4/1974 | Kerley et al. | 44/76 X |
| 4,127,654 | 11/1978 | Inoue et al. | 252/48.2 X |

*Primary Examiner*—Andrew Metz
*Attorney, Agent, or Firm*—Donald L. Johnson; Robert A. Linn; Joseph D. Odenweller

[57] ABSTRACT

Engine friction of internal combustion engines is reduced by adding to the lubricating oil or fuel used in such engine a small friction-reducing amount of an aliphatic hydrocarbylsulfonylalkanol or aliphatic hydrocarbylsulfinylalkanol resulting in improved fuel economy.

22 Claims, No Drawings

LUBRICATING OIL AND FUEL COMPOSITIONS

BACKGROUND OF THE INVENTION

In order to conserve energy, automobiles are now being engineered to give improved gasoline mileage compared to those in recent years. This effort is of great urgency as a result of Federal regulations recently enacted which compel auto manufacturers to achieve prescribed gasoline mileage. These regulations are to conserve crude oil. In an effort to achieve the required mileage, new cars are being down-sized and made much lighter. However, there are limits in this approach beyond which the cars will not accommodate a typical family.

Another way to improve fuel mileage is to reduce engine friction. The present invention is concerned with this latter approach.

SUMMARY

According to the present invention it has been discovered that the operating friction of an internal combustion engine can be reduced by adding to the lubricating oil or fuel used in such engine a minor amount of an aliphatic hydrocarbylsulfonylalkanol or aliphatic hydrocarbylsulfinylalkanol.

DESCRIPTION OF THE PREFERRED EMBODIMENTS

A preferred embodiment of the invention is a lubricating oil or liquid hydrocarbon fuel containing a minor amount sufficient to reduce engine friction of an additive selected from the group consisting of oil soluble and fuel soluble aliphatic hydrocarbylsulfinylalkanols and aliphatic hydrocarbylsulfonylalkanols, said additive having the structure:

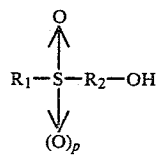

wherein $R_1$ is an aliphatic hydrocarbon group containing about 12–36 carbon atoms, $R_2$ is a divalent aliphatic hydrocarbon group containing 1 to about 4 carbon atoms and p is 0 or 1.

In the above formula $R_1$ can be straight chain, branched chain, primary, secondary, tertiary, saturated, or olefinically unsaturated hydrocarbon groups. Examples of suitable groups are n-dodecyl, 2-ethyldecyl, 1-methylundecyl, 1,1-dimethyldecyl, n-tetradecyl, 2-butyldecyl, n-hexadecyl, 2-butylhexadecyl, 1-ethyltetradecyl, n-eicosyl, 1-ethyleicosyl, 1-butyleicosyl, n-docosyl, 1-butyldocosyl, n-triacontyl, 1-ethyltriacontyl, n-hexatriacontyl, n-dodecenyl, 2-ethyldecenyl, 1-methylheptadecenyl and the like. Highly preferred groups are hexadecyl and octadecyl.

In one preferred embodiment p is 0, such that the additives are aliphatic hydrocarbylsulfinylalkanols. Examples of these additives are:
2-(dodecylsulfinyl)ethanol
2-(2-ethyldodecylsulfinyl)ethanol tetradecylsulfinylmethanol
2-(1-butyldodecylsulfinyl)propanol
2-(1-ethyloctadecylsulfinyl)butanol
3-(1-methyldocosylsulfinyl)propanol and the like.

In this embodiment the more preferred additives are $C_{16}$ hydrocarbylsulfinylalkanols and $C_{18}$ hydrocarbylsulfinylalkanols and mixtures thereof. Representative examples of these are:
2-(hexadecylsulfinyl)ethanol
2-(octadecylsulfinyl)ethanol
2-(2-ethyltetradecylsulfinyl)propanol
2-(1-methylheptadecylsulfinyl)ethanol
2-(1-methylpentadecylsulfinyl)butanol
and the like.

In another preferred embodiment p is 1, such that the additives are aliphatic hydrocarbylsulfonylalkanols. Representative examples of these are:
2-(dodecylsulfonyl)ethanol
3-(tetradecylsulfonyl)propanol
2-(2-ethyldodecylsulfonyl)propanol
2-(1-methylheptadecylsulfonyl)ethanol
2-(hexadecenylsulfonyl)propanol
4-(1-methylheptadecenylsulfonyl)butanol
2-(eicosylsulfonyl)ethanol
2-(hexacosylsulfonyl)ethanol
2-(hexatriacontylsulfonyl)butanol
and the like.

In this embodiment the more preferred compounds are $C_{16}$ and $C_{18}$ aliphatic hydrocarbylsulfonylalkanols. Representative examples of these are:
2-(hexadecylsulfonyl)ethanol
2-(1-methylpentadecylsulfonyl)ethanol
2-(1-methylheptadecylsulfonyl)propanol
2-(1-hexyldodecylsulfonyl)ethanol
2-(octadecylsulfonyl)ethanol
and the like.

In a highly preferred embodiment $R_2$ is the group —$CH_2$—$CH_2$— such that the additives are ethanol derivatives. Representative examples of these are:
2-(hexadecylsulfonyl)ethanol
2-(hexadecenylsulfonyl)ethanol
2-(1-butyldodecylsulfinyl)ethanol
2-(1-ethyltetradecylsulfinyl)ethanol
2-(1-methylheptadecylsulfinyl)ethanol
2-(1-methylheptadecenylsulfinyl)ethanol
2-(2-ethylhexadecylsulfonyl)ethanol
2-(octadecylsulfinyl)ethanol The most preferred additives are:
2-(hexadecylsulfinyl)ethanol
2-(octadecylsulfinyl)ethanol
2-(hexadecylsulfonyl)ethanol
2-(octadecylsulfonyl)ethanol The additives are readily made by conventional methods by first making an aliphatic hydrocarbylthioalkanol. These can be made by reaction of an olefinically unsaturated hydrocarbon with a mercaptoalkanol under uv radiation. This is then oxidized with hydrogen peroxide to form the sulfinyl or sulfonyl derivative depending upon the degree of oxidation. Generally, an equal mole amount of hydrogen peroxide will form the sulfinyl derivative and two moles of hydrogen peroxide per mole of hydrocarbylthioalkanol will form the sulfonyl derivative. Intermediate amounts will form mixtures which are also useful.

The following example illustrates the preparation of representative compounds.

EXAMPLE 1

Preparation of Hydrocarbylsulfinylalkanols

In a uv cell was placed 30 grams of a mixture of 50 weight percent α-hexadecene and 50 weight percent α-octadecene and 10 grams of mercaptoethanol. The mixture was stirred 30 minutes under uv radiation leaving 40 grams of a mixture of 2-(octadecylthio)ethanol and 2-(hexadecylthio)ethanol.

In a second reaction vessel was placed 75 grams of the above mixture, 100 ml methanol, 3 grams sodium bromide and 5 ml acetic acid. Then 32 grams of 30% hydrogen peroxide was added dropwise at 45°–50° C. over a 30-minute period. The methanol was then distilled off and about 200 ml of heptane was added. The heptane was distilled off to remove water. The sodium bromide precipitate was then filtered at about 75° C. The filtrate was cooled forming a precipitate. This was filtered off to yield 45 grams of 2-($C_{16-18}$ alkylsulfinyl) ethanol.

Other similar sulfinyl derivatives can be made following the above general procedure by using different aliphatic hydrocarbylthioalkanols.

EXAMPLE 2

Preparation of Hydrocarbylsulfonylalkanols

To a uv cell was added 429 grams of 1-octadecene and 135 grams of mercaptoethanol. This mixture was stirred 60 minutes under uv radiation. Following this, the unreacted mercaptoethanol was distilled out leaving 535 grams of 1-octadecylthioethanol.

In a reaction vessel was placed 450 grams of 1-octadecylthioethanol and 500 ml methanol. While stirring 309 grams of 30% hydrogen peroxide was added dropwise over a 45-minute period at 45°–50° C. The mixture was then heated to 70° C. and stirred for one hour. It was then vacuum distilled to 100° C. at 30 mm Hg abs to remove methanol and water yielding 478 grams of 2-(octadecylsulfonyl)ethanol.

Other similar sulfonyl derivatives can be made following the above general procedure using other aliphatic hydrocarbylthioalkanols.

The additives are added to lubricating oil in an amount which reduces the friction of an engine operating with the oil in the crankcase. A useful concentration is about 0.05–3 weight percent. A more preferred range is about 0.1–1.5 weight percent.

From the above it can be seen that the present invention provides an improved crankcase lubricating oil. Accordingly, an embodiment of the invention is an improved motor oil composition formulated for use as a crankcase lubricant in an internal combustion engine wherein the improvement comprises including in the crankcase oil an amount sufficient to reduce fuel consumption of the engine of an aliphatic hydrocarbylsulfinyl or sulfonyl alkanol.

In a highly preferred embodiment such improved motor oil also contains an ashless dispersant, a zinc dialkyldithiophosphonate and an alkaline earth metal salt of a petroleum sulfonic acid or an alkaryl sulfonic acid (e.g. alkylbenzene sulfonic acid).

The additives can be used in mineral oil or in synthetic oils of viscosity suitable for use in the crankcase of an internal combustion engine. Crankcase lubricating oils have a viscosity up to about 80 SUS at 210° F. According to the present invention the additives function to increase fuel economy when added to lubricating oil compositions formulated for use in the crankcase of internal combustion engines. Similar mileage benefits could be obtained in both spark ignited and diesel engines.

Crankcase lubricating oils of the present invention have a viscosity up to about SAE 40. Sometimes such motor oils are given a classification of both 0° and 210° F., such as SAE 10W 40 or SAE 5W 30.

Crankcase lubricants of the present invention can be further identified since they usually contain a zinc dihydrocarbyldithiophosphate in addition to the present additive. Likewise, these crankcase lubricants contain an alkaline earth metal sulfonate such as calcium petroleum sulfonate, calcium alkaryl sulfonate, magnesium petroleum sulfonate, magnesium alkaryl sulfonate, barium petroleum sulfonate, barium alkaryl sulfonate and the like.

Mineral oils include those of suitable viscosity refined from crude oil from all sources including Gulfcoast, midcontinent, Pennsylvania, California, Alaska and the like. Various standard refinery operations can be used in processing the mineral oil.

Synthetic oil includes both hydrocarbon synthetic oil and synthetic esters. Useful synthetic hydrocarbon oils include liquid polymers of α-olefins having the proper viscosity. Especially useful are the hydrogenated liquid oligomers of $C_{6-12}$ α-olefins such as α-decene trimer. Likewise, alkylbenzenes of proper viscosity can be used, such as didodecylbenzene.

Useful synthetic esters include the esters of both monocarboxylic acid and polycarboxylic acid as well as monohydroxy alkanols and polyols. Typical examples are didodecyl adipate, trimethylol propane tripelargonate, pentaerythritol tetracaproate, di-(2-ethylhexyl)adipate, dilauryl sebacate and the like. Complex esters prepared from mixtures of mono- and dicarboxylic acid and mono- and polyhydroxyl alkanols can also be used.

Blends of mineral oil with synthetic oil are particularly useful. For example, blends of 10–25 weight percent hydrogenated α-decene trimer with 75–90 weight percent 150 SUS (100° F.) mineral oil results in an excellent lubricant. Likewise, blends of about 10–25 weight percent di-(2-ethylhexyl)adipate with mineral oil of proper viscosity results in a superior lubricating oil. Also blends of synthetic hydrocarbon oil with synthetic esters can be used. Blends of mineral oil with synthetic oil are especially useful when preparing low viscosity oil (e.g. SAE 5W 20) since they permit these low viscosities without contributing excessive volatility.

The more preferred lubricating oil composition includes zinc dihydrocarbyldithiophosphate (ZDDP) in combination with the present additives. Both zinc dialkyldithiophosphates and zinc dialkaryldithiophosphates as well as mixed alkyl-aryl ZDDP are useful. A typical alkyl-type ZDDP contains a mixture of isobutyl and isoamyl groups. Zinc dinonylphenyldithiophosphate is a typical aryl-type ZDDP. Good results are achieved using sufficient ZDDP to provide about 0.01–0.5 weight percent zinc. A preferred concentration supplies about 0.05–0.3 weight percent zinc.

Another additive used in the oil compositions are the alkaline earth metal petroleum sulfonates or alkaline earth metal alkaryl sulfonates. Examples of these are calcium petroleum sulfonates, magnesium petroleum sulfonates, barium alkaryl sulfonates, calcium alkaryl sulfonates or magnesium alkaryl sulfonates. Both the neutral and the overbased sulfonates having base numbers up to about 400 can be beneficially used. These are used in an amount to provide about 0.05–1.5 weight percent alkaline earth metal and more preferably about 0.1–1.0 weight percent. In a most preferred embodiment the lubricating oil composition contains a calcium petroleum sulfonate or alkaryl (e.g. alkylbenzene) sulfonate.

Viscosity index improvers can be included such as the polyalkylmethacrylate type or the ethylene-propylene copolymer type. Likewise, styrene-diene VI improvers or styrene-acrylate copolymers can be used. Alkaline earth metal salts of phosphosulfurized polyisobutylene are useful.

Most preferred crankcase oils also contain an ashless dispersant such as the polyolefin-substituted succinamides and succinimides of polyethylene polyamines such as tetraethylenepentamine. The polyolefin succinic substituent is preferably a polyisobutene group having a molecular weight of from about 800 to 5,000. Such ashless dispersants are more fully described in U.S. Pat. Nos. 3,172,892 and 3,219,666 incorporated herein by reference.

Another useful class of ashless dispersants are the polyolefin succinic esters of mono- and polyhydroxy alcohols containing 1 to about 40 carbon atoms. Such dispersants are described in U.S. Pat. Nos. 3,381,022 and 3,522,179.

Likewise, mixed ester/amides of polyolefin substituted succinic acid made using alkanols, amines and/or aminoalkanols represent a useful class of ashless dispersants.

The succinic amide, imide and/or ester type ashless dispersants may be boronated by reaction with a boron compound such as boric acid. Likewise the succinic amide, imide, and/or ester may be oxyalkylated by reaction with an alkylene oxide such as ethylene oxide or propylene oxide.

Other useful ashless dispersants include the Mannich condensation products of polyolefin-substituted phenols, formaldehyde and polyethylene polyamine. Preferably, the polyolefin phenol is a polyisobutylene-substituted phenol in which the polyisobutylene group has a molecular weight of from about 800 to 5,000. The preferred polyethylene polyamine is tetraethylene pentamine. Such Mannich ashless dispersants are more fully described in U.S. Pat. Nos. 3,368,972; 3,413,347; 3,442,808; 3,448,047; 3,539,633; 3,591,598; 3,600,372; 3,634,515; 3,697,574; 3,703,536; 3,704,308; 3,725,480; 3,726,882; 3,736,357; 3,751,365; 3,756,953; 3,793,202; 3,798,165; 3,798,247 and 3,803,039.

The above Mannich dispersants can be reacted with boric acid to form boronated dispersants having improved corrosion properties.

Superior results are obtained by using the aliphatic hydrocarbylsulfinylalkanols and aliphatic hydrocarbylsulfonylalkanols in lubricating oil in combination with a phosphonate additive. Preferred phosphonates are the di-$C_{1-4}$ alkyl $C_{12-36}$ alkyl or alkenyl phosphonates. These compounds have the structure:

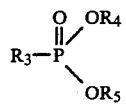

wherein $R_3$ is an aliphatic hydrocarbon group containing about 12–36 carbon atoms and $R_4$ and $R_5$ are independently selected from lower alkyl groups containing about 1–4 carbon atoms. Representative examples of these synergistic coadditives are:
dimethyl octadecylphosphonate
dimethyl octadecenylphosphonate
diethyl 2-ethyldecylphosphonate
ethyl propyl 1-butylhexadecylphosphonate
methyl ethyl octadecylphosphonate
methyl butyl eicosylphosphonate
dimethyl hexatriacontylphosphonate When using the phosphonate coadditive only a small synergistic amount is required. A useful range is about 0.005–0.75 weight percent based on the formulated oil. A more preferred amount is about 0.05–0.5 weight percent.

The friction reducing additives of this invention are also useful in fuel compositions. Fuel injected or inducted into a combustion chamber wets the walls of the cylinder. Fuels containing a small amount of the present additive reduce the friction due to the piston rings sliding against the cylinder wall.

The additives can be used in both diesel fuel and gasoline used to operate internal combustion engines. Fuels containing about 0.001–0.25 weight percent of the sulfonyl or sulfinyl derivatives can be used.

Fuels used with the invention can contain any of the additives conventionally added to such fuels. In the case of gasoline it can include dyes, antioxidants, detergents, antiknocks (e.g. tetraethyllead, methylcyclopentadienylmanganese tricarbonyl, rare earth metal chelates, methyl tert-butylether and the like). In the case of diesel fuels the compositions can include pour point depressants, detergents, ignition improvers (e.g. hexylnitrate) and the like.

Tests were conducted which demonstrated the friction reducing properties of the present invention.

LFW-1 Test

In this test a metal cylinder is rotated around its axis 45° in one direction and then 45° in the opposite direction at a rate of 120 cycles per minute. A metal block curved to conform to the circular contour of the cylinder presses at a fixed load against the periphery of the cylinder. Test lubricant is applied to the rubbing surface between the cylinder and the block. Torque transmitted to the block from the oscillating cylinder is measured. The greater the torque the greater the friction. Results are given in terms of "percent improvement" which is the percent reduction in torque compared to that obtained with the test oil without the test additive.

SAE-2 Fly Wheel Test

In this test a heavy fly wheel is rotated at 1440 rpm. A series of 9 clutch plates are then brought to bear axially at a defined load against the fly wheel. The fly wheel is connected to the rotating plate. The static plates are connected to a device which measures rotational torque. The time from initially applying pressure through the clutch plate until the rotating plates stop rotating is measured. Also, the rotational torque measured at the static plates is plotted against time. Torque rises to a value preferred to as "dynamic torque" and then rises to a maximum called "static torque" as the plates stop rotation. The clutch plates are immersed in test lubricant. A reduction in friction is indicated by (1) an increase in time required to stop the rotation of the moving plates and (2) a decrease in dynamic and static torque. Results are reported in percent time increase (percent improvement) and percent reduction in torque compared to that obtained using the same oil without the test additive.

The test oil is a fully formulated oil of SAE SE quality. Test results are given in the following table:

| Additive | LFW-1 % Improvement | SAE No. 2 % Improvement | | |
|---|---|---|---|---|
| | | Time Increase | Dyn. | Static |
| C$_{16-18}$ alkylsulfinylethanol (0.15%) | 14 | 9 | 14 | 39 |
| C$_{16-18}$ alkylsulfinylethanol (0.15%) plus dimethyl octadecylphosphonate (0.2%) | 20 | — | — | — |
| C$_{16-18}$ alkylsulfonylethanol (0.3%) | 11 | 10 | 13 | 38 |
| C$_{16-18}$ alkylsulfonylethanol (0.3%) plus dimethyl octadecylphosphonate (0.2%) | 14 | 14 | 17 | 35 |
| Dimethyl octadecylphosphonate (0.3%) | 11 | 8.8 | 13.7 | 30.3 |
| Dimethyl octadecylphosphonate (0.5%) | 11.5 | 9.9 | 16.1 | 40.9 |

The above results show that both the sulfinyl and sulfonyl additives are very effective in reducing friction and that their effectiveness is improved by use in combination with a phosphonate.

We claim:

1. In a lubricating oil composition formulated for use in the crankcase of an internal combustion engine, said composition comprising a major amount of an oil of lubricating viscosity, the improvement of including in the composition a friction-reducing amount of an additive having the structure:

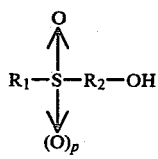

wherein R$_1$ is an aliphatic hydrocarbon group containing about 12-36 carbon atoms, R$_2$ is a divalent saturated aliphatic hydrocarbon group containing 1 to about 4 carbon atoms and p is 0 or 1, said improvement resulting in increased fuel economy.

2. A lubricating oil composition of claim 1 wherein p is 0 such that said additive is an aliphatic hydrocarbylsulfinylalkanol.

3. A lubricating oil composition of claim 2 wherein R$_2$ is the group —CH$_2$—CH$_2$—.

4. A lubricating oil composition of claim 3 wherein R$_1$ is an aliphatic hydrocarbon group consisting mainly of groups containing 16-18 carbon atoms.

5. A lubricating oil composition of claim 1 wherein p is 1 such that said additive is a hydrocarbylsulfonylalkanol.

6. A lubricating oil composition of claim 5 wherein R$_2$ is the group —CH$_2$—CH$_2$—.

7. A lubricating oil composition of claim 6 wherein R$_1$ is an aliphatic hydrocarbon group consisting mainly of groups containing 18 carbon atoms.

8. A lubricating oil composition of claim 1 further characterized by containing a minor amount, sufficient to further reduce friction, of a di-C$_{1-4}$ alkyl C$_{12-36}$ alkylphosphonate.

9. A lubricating oil composition of claim 8 wherein said di-C$_{1-4}$ alkyl C$_{12-36}$ alkylphosphonate is a dimethyl C$_{12-36}$ alkylphosphonate.

10. A lubricating oil composition of claim 9 wherein said dimethyl C$_{12-36}$ alkylphosphonate is dimethyl octadecylphosphonate.

11. A lubricating oil composition of claim 2 containing a minor amount, sufficient to further reduce friction, of a di-C$_{1-4}$ alkyl C$_{12-36}$ alkylphosphonate.

12. A lubricating oil composition of claim 11 wherein said di-C$_{1-4}$ alkyl C$_{12-36}$ alkylphosphonate is a dimethyl C$_{12-36}$ alkylphosphonate.

13. A lubricating oil composition of claim 12 wherein said dimethyl C$_{12-36}$ alkylphosphonate is dimethyl octadecylphosphonate.

14. A lubricating oil composition of claim 13 wherein said hydrocarbylsulfinylalkanol is 2-(C$_{16-18}$ alkylsulfinyl) ethanol.

15. A lubricating oil composition of claim 5 containing a minor amount, sufficient to further reduce friction, of a di-C$_{1-4}$ alkyl C$_{12-36}$ alkylphosphonate.

16. A lubricating oil composition of claim 15 wherein said di-C$_{1-4}$ alkyl C$_{12-36}$ alkylphosphonate is a dimethyl C$_{12-36}$ alkylphosphonate.

17. A lubricating oil composition of claim 16 wherein said dimethyl C$_{12-36}$ alkylphosphonate is dimethyl octadecylphosphonate.

18. A lubricating oil composition of claim 17 wherein said hydrocarbylsulfonylalkanol is octadecylsulfonyl ethanol.

19. A liquid hydrocarbon fuel suitable for use in internal combustion engines containing a minor friction-reducing amount of an additive selected from the group consisting of fuel-soluble aliphatic hydrocarbylsulfonylalkanols, said additive having the structure:

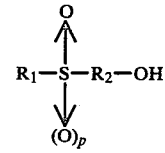

wherein R$_1$ is an aliphatic hydrocarbon group containing about 12-36 carbon atoms, R$_2$ is a divalent aliphatic hydrocarbon group containing 1 to about 4 carbon atoms and p is 1.

20. A composition of claim 19 wherein said liquid hydrocarbon fuel is gasoline suitable for use in a spark ignited internal combustion engine.

21. A composition of claim 20 wherein R$_2$ is the group —CH$_2$—CH$_2$—.

22. A composition of claim 21 wherein R$_1$ is an aliphatic hydrocarbon group consisting mainly of groups containing 18 carbon atoms.

* * * * *